(12) United States Patent
Licht et al.

(10) Patent No.: US 6,475,947 B1
(45) Date of Patent: Nov. 5, 2002

(54) OLIGOMERIC METALLOCENES AND THEIR USE

(75) Inventors: Erik Licht, Bayreuth (DE); Helmut G. Alt, Bayreuth (DE); M. Bruce Welch, Bartlesville, OK (US); Bryan E. Hauger, Claremore, OK (US)

(73) Assignee: Phillips Petroleum Company, Bartlesville, OK (US)

( * ) Notice: Subject to any disclaimer, the term of this patent is extended or adjusted under 35 U.S.C. 154(b) by 0 days.

(21) Appl. No.: 09/393,796

(22) Filed: Sep. 10, 1999

(51) Int. Cl.$^7$ .......................... B01J 31/00; B01J 37/00; C08F 4/02; C08F 4/44; C08F 4/60
(52) U.S. Cl. ................ 502/117; 502/152; 502/155; 556/11; 556/53; 526/134; 526/160; 526/943
(58) Field of Search .................. 502/117; 556/53, 556/11; 526/134, 160, 943

(56) References Cited

U.S. PATENT DOCUMENTS

| | | | | |
|---|---|---|---|---|
| 5,071,808 A | | 12/1991 | Antberg et al. ............. 502/107 |
| 5,153,157 A | | 10/1992 | Hlatky et al. ................ 502/117 |
| 5,308,817 A | * | 5/1994 | Reddy et al. ................ 502/102 |
| 5,498,581 A | | 3/1996 | Welch et al. ................ 502/102 |
| 5,561,092 A | | 10/1996 | Ewen et al. ................. 502/117 |
| 5,587,501 A | * | 12/1996 | Winter et al. ................. 556/53 |
| 5,747,405 A | * | 5/1998 | Little et al. ................. 502/113 |
| 5,770,538 A | | 6/1998 | Devore et al. ............. 502/117 |
| 5,854,363 A | * | 12/1998 | Jung et al. .................. 502/103 |
| 5,886,202 A | * | 3/1999 | Jung et al. .................. 526/121 |
| 6,002,032 A | * | 12/1999 | Erker et al. ................... 556/11 |
| 6,239,300 B1 | * | 5/2001 | Stouffer et al. ............. 502/103 |
| 6,340,651 B1 | * | 1/2002 | Licht et al. | |

FOREIGN PATENT DOCUMENTS

WO     WO 98/52686     * 11/1998

* cited by examiner

Primary Examiner—Elizabeth D. Wood
(74) Attorney, Agent, or Firm—McDermott, Will & Emery

(57) ABSTRACT

A process for producing a new metallocene comprising reacting a first bridged metallocene which has an olefinically unsaturated with about two molar equivalents of an alkali metal alkyl, catalyst systems resulting from the combination of the resulting metallocenes and a cocatalyst, and polymerization processes using such catalyst systems are disclosed.

10 Claims, No Drawings

OLIGOMERIC METALLOCENES AND THEIR USE

BACKGROUND OF THE INVENTION

Metallocenes have been found to be useful for the polymerization of olefins. In order for metallocenes to be particularly useful in slurry type polymerization processes, it has generally been found necessary to form a catalyst system in which the metallocene and the cocatalyst are insoluble during the polymerization. Various approaches have been taken to provide insoluble heterogeneous catalyst systems that would be applicable. One technique involves the employment of metallocenes containing unsaturated substituents which can be prepolymerized in the presence of a cocatalyst to produce a solid insoluble catalyst system. An example of such a process is disclosed in U.S. Pat. No. 5,498,581. Another approach for preparing such an insoluble heterogeneous catalyst system involves the employment of a special type of metallocene referred to as a metallocycle metallocene. A metallocycle type metallocene is one in which one of the cyclodienyl groups that is pi bonded to the metal of the metallocene also contains a substituent which is sigma bonded to the metal of the metallocene. An example of such a metallocene is disclosed in U.S. Pat. No. 5,654,454. In that case, the metallocycle was produced by a hydrozirconation type reaction. Such compounds are often referred to as metallocycles for the reason that there is what can be viewed as a cyclic structure comprising the cyclic dienyl group pi bonded to the zirconium and the substituent on the cyclic dienyl group being sigma bonded to the metal.

In accordance with the present invention, there is provided a process for producing a new type of metallocene which could be called an oligomeric metallocycle metallocene. The term oligomeric metallocene as used herein refers to a metallocene which has a plurality of repeating units which are bridged metallocenes wherein each unit is connected to the other through a cyclic structure connecting the bridge of one unit to the metal of the next unit.

An object of the present invention is to provide catalyst systems using such oligomeric metallocenes and polymerization processes using such catalyst systems.

Another object of the present invention is to provide a metallocene which can be prepolymerized to form a solid particulate catalyst system suitable for use in slurry polymerization processes.

SUMMARY OF THE INVENTION

In accordance with the present invention, there is provided a process for producing oligomeric metallocenes which involves reacting a first bridged metallocene having an alkenyl group attached to the bridge with an alkali metal alkyl. Still further in accordance with the present invention, there is provided a process for polymerizing olefins using such metallocenes. Still further in accordance with the present invention, there is provided a process for employing such metallocenes to produce catalyst systems useful for the polymerization of olefins. In a particularly preferred process, the metallocenes are used to form a prepolymerized heterogeneous catalyst that is suitable for use in a slurry type olefin polymerization process.

DETAILED DESCRIPTION OF THE INVENTION

In accordance with the present invention, the new metallocenes are prepared by reacting a first bridged metallocene having an alkenyl group attached to the bridge group with about two molar equivalents of an alkali metal alkyl having at least 4 carbon atoms. Preferably the alkenyl group is an ω-alkenyl group with terminal unsaturation having 3–10 carbon atoms.

It is contemplated that the process can be applied to any metallocene in which there is a cyclodienyl group which has the required type of alkenyl substituted bridging radical. The currently preferred metallocenes are those of the transition metal compounds Ti, Zr, and Hf. Examples of such metallocenes would include those of the formula

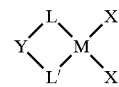

wherein L and L' are the same or different radicals having a cyclodienyl skeleton, examples of which would include cyclopentadienyl, indenyl, fluorenyl, and benzo indenyl, both substituted and unsubstituted; Y is a structural unit connecting L to L', Y being further characterized by having a substituent with olefin unsaturation, preferably having 3 to 20 carbons, and M is a transition metal, preferably Zr, Hf, or Ti. Examples of Y include alkylidene and silylene divalent radicals preferably having 4 to 20 carbon atoms. Some specific examples of Y would be —$CR_2$—, —$SiR_2$—, and the like, wherein one R is a hydrocarbyl radical having olefinic functionality and 3 to 8 carbon atoms and the other R is selected from hydrogen and hydrocarbyl radicals having 1 to 10 carbon atoms. Each X can be the same or different and is selected from halogens and organo radicals having 1 to 20 carbon atoms. Preferably X is selected from halogens, alkyl, aryl, alkaryl, and alkoxy radicals.

The substituents on L and L', if any, are preferably hydrocarbyl substituents having 1 to 20 carbon atoms, more preferably 1 to 5 carbon atoms.

The reaction of the first metallocene and the alkali metal alkyl can be conducted in any suitable manner. Typically the reaction would be carried out by forming a solution of the metallocene in a hydrocarbon, for example toluene, and then adding a solution of the alkali metal alkyl. The temperature employed can vary widely; however, temperatures below 0° C. are generally preferred for the combining the metallocene and the alkali metal alkyl, for example 0 to –90° C., more typically –20° C. to –80° C.

The resulting oligomeric metallocycle metallocene can be used for polymerization reactions. The inventive catalyst systems are particularly useful for the polymerization of alpha-olefins having 2 to 10 carbon atoms. Examples of such olefins include ethylene, propylene, butene-1, pentane-1, 3-methylbutene-1, hexene-1, 4-methylpentene-1, 3-methylpentene-1, heptene-1, octene-1, decene-1, 4,4-dimethyl-1-pentane, 4,4-diethyl-1-hexene, 3,4-dimethyl-1-hexene, and the like and mixtures thereof. The catalysts are also useful for preparing copolymers of ethylene and propylene and copolymers of ethylene or propylene and a higher molecular weight olefin. Monomers such as styrene and butadiene are also useful.

Polymerizations with the inventive catalyst can be carried out under a wide range of conditions depending upon the particular metallocene employed and the particular results desired. The inventive catalyst systems are considered useful for polymerization conducted under solution, slurry, or gas phase reaction conditions. Typically the inventive metallocene would be used with a suitable cocatalyst.

Examples of suitable cocatalysts include generally any of those organometallic cocatalysts which have in the past been employed in conjunction with transition metal containing olefin polymerization catalysts. Some typical examples include organometallic compounds of metals of Groups IA, IIA, and IIIB of the Periodic Table. Examples of such compounds have included organometallic halide compounds, organometallic hydrides and even metal hydrides. Some specific examples include triethylaluminum, triisobutylaluminum, diethylaluminum chloride, diethylaluminum hydride, and the like. Other examples of known cocatalysts include the use of a stable non-coordinating counter anion cocatalyst, an example of such is disclosed in U.S. Pat. No. 5,155,080, e.g. using triphenyl carbenium tetrakis(pentafluorophenyl)boronate. Another example would be the use of a mixture of trimethylaluminum and dimethylfluoroaluminum such as disclosed by Zambelli et al, *Macromolecules* 22, 2186 (1989). In such counter anion systems, the cocatalyst can be viewed as an ion-exchange compound comprising a cation which will irreversibly react with at least one ligand contained in the metallocene and a non-coordination anion which is either a single coordination complex comprising a plurality of lipophilic radicals covalently coordinated to and shielding a central formally charge-bearing metal or metalloid atom or an anion comprising a plurality of boron atoms such as polyhedral boranes, carboranes, and metallacarboranes.

A currently preferred boron containing cocatalyst is tris (perfluorophenyl)borane, i.e. $B(C_6F_5)_3$, which is a simpler cocatalyst than the salt type boron cocatalysts.

Another currently preferred cocatalyst is an aluminoxane. Such compounds include those compounds having repeating units of the formula

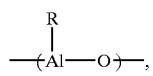

where R is generally a hydrocarbyl group having 1 to 5 carbon atoms. The organo aluminoxane component used in preparing the inventive solid catalyst system include oligomeric aluminum compounds having repeating units of the formula

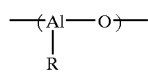

Some examples are often represented by the general formula $(R\text{—}Al\text{—}O)_n$ or $R(R\text{—}Al\text{—}O\text{—})_nAlR^2$. In the general aluminoxane formula R is preferably a $C_1$–$C_5$ alkyl radical, for example, methyl, ethyl, propyl, butyl or pentyl and "n" is an integer from 1 to about 50. Most preferably, R is methyl and "n" is at least 4.

Aluminoxanes can be prepared by various procedures known in the art. For example, an aluminum alkyl may be treated with water dissolved in an inert organic solvent, or it may be contacted with a hydrated salt, such as hydrated copper sulfate suspended in an inert organic solvent, to yield an aluminoxane. Generally the reaction of an aluminum alkyl with a limited amount of water is postulated to yield a mixture of the linear and cyclic species of the aluminoxane. Aluminoxanes, also sometimes referred to as poly (hydrocarbyl aluminum oxides) are well known in the art and are generally prepared by reacting a hydrocarbylaluminum compound with water. Such preparation techniques are disclosed in U.S. Pat. Nos. 3,242,099 and 4,808,561, the disclosures of which are incorporated herein by reference. The currently preferred aluminoxane cocatalysts are prepared either from trimethylaluminum or triethylaluminum and are sometimes referred to as poly(methyl aluminum oxide) and poly(ethyl aluminum oxide), respectively. It is also within the scope of the invention to use an aluminoxane in combination with a trialkylaluminum, such as disclosed in U.S. Pat. No. 4,794,096, the disclosure of which is incorporated herein by reference.

In a particular preferred embodiment, the inventive metallocene can be employed in combination with a solid organoaluminoxane which is substantially insoluble in the polymerization diluent under particle form polymerization conditions. Such a solid aluminoxane can be prepared by contacting a solution of an organoaluminoxane with an organoboroxine under conditions sufficient to produce a solid. Another technique for preparing an insoluble organoaluminoxane involves contacting a solution of an organoaluminoxane with water or an active hydrogen compound as taught in U.S. Pat. No. 4,990,640.

Still another technique of producing a solid cocatalyst involves contacting an organoaluminoxane with an organic borane compound free of acidic hydrogen as taught in U.S. Pat. No. 5,354,721, the disclosure of which is incorporated herein by reference. Yet another technique involves contacting an organoaluminoxane with an organoboron compound having boron acid functionality, i.e. —BOH, as taught in U.S. Pat. No. 5,414,189, the disclosure of which is incorporated herein by reference.

The currently preferred technique for preparing the solid organoaluminoxy cocatalyst involves contacting an organic solution of an organoaluminoxane optionally containing trialkylaluminums with a suitable organoboroxine compound as taught in U.S. Pat. No. 5,411,925, the disclosure of which is incorporated herein by reference.

When the polymerizations are carried out in the presence of liquid diluents, obviously it is important to use diluents which do not have an adverse effect upon the catalyst system. Typical liquid diluents include propane, butane, isobutane, pentane, hexane, heptane, octane, cyclohexane, methylcyclohexane, toluene, xylene, and the like. Typically the polymerization temperature can vary over a wide range, temperatures typically would be in a range of about −60° C. to about 300° C., more preferably in the range of about 20° C. to about 160° C. Typically the pressure of the polymerization would be in the range of from about 1 to about 500 atmospheres or even greater. The inventive catalyst system is particularly useful for polymerizations carried out under particle form, i.e., slurry-type polymerization conditions.

In a particularly preferred embodiment of the present invention, the inventive metallocene is combined with a cocatalyst and subjected to prepolymerization with an olefin to produce a solid catalyst system that can later be used in the polymerization of olefins. This technique is particularly useful in slurry or particle-form type polymerizations.

To prepare the solid prepolymerized catalyst system the metallocene and cocatalyst are combined in the presence of a suitable liquid to form a liquid catalyst system. It is preferred that the liquid catalyst system be prepared using an organic liquid in which the cocatalyst is at least partially soluble. The currently preferred liquids are hydrocarbons such as hexane or toluene. Typically an aromatic liquid solvent is employed. Examples include benzene, toluene, ethylbenzene, diethylbenzene, and the like. The amount of liquid to be employed is not particularly critical. Nevertheless, the amount should preferably be such as to dissolve at least a portion of the product of the reaction between the metallocene and the cocatalyst, provide desirable polymerization viscosity for the prepolymerization, and to permit good mixing. The temperature is preferably kept below that which would cause the metallocene to decompose. Typically the temperature would be in the range of −50° C. to 100° C. Preferably, the metallocene, the cocatalyst, and the liquid diluent are combined at room temperature or slightly under room temperature, i.e. a temperature in the range of about 0 to 30° C. The reaction between the cocatalyst and the metallocene is relatively rapid. The reaction rate can vary depending upon the ligands of the metallocene. It is generally desired that they be contacted for at least about a minute to about 1 hour.

It is within the scope of the invention to form the liquid catalyst system in the presence of a particulate solid. Any number of particulate solids can be employed as the particulate solid. Typically the support can be any organic or inorganic solid that does not interfere with the desired end result. Examples include porous supports such as talc, inorganic oxides, and resinous support materials such as particulate polyolefins. Examples of inorganic oxide materials include Groups II, III, IV or V metal oxides such as silica, alumina, silica-alumina, and mixtures thereof. Other examples of inorganic oxides are magnesia, titania, zirconia, and the like. Other suitable support materials which can be employed include materials such as, magnesium dichloride, and finely divided polyolefins, such as polyethylene. It is within the scope of the present invention to use a mixture of one or more of the particulate solids. If a particulate solid, i.e. silica, is used generally it is used in an amount such that the weight ratio of the metallocene to the particulate solid is in the range of about 0.00001/1 to 1/1, more preferably 0.0005/1 to 0.2/1.

It is generally desirable for the solid to be thoroughly dehydrated prior to use, preferably it is dehydrated so as to contain less than 1% loss on ignition. Thermal dehydration treatment may be carried out in vacuum or while purging with a dry inert gas such as nitrogen at a temperature of about 20° C. to about 1000° C., and preferably, from about 300° C. to about 800° C. Pressure considerations are not critical. The duration of thermal treatment can be from about 1 to about 24 hours. However, shorter or longer times can be employed provided equilibrium is established with the surface hydroxyl groups.

Dehydration can also be accomplished by subjecting the solid to a chemical treatment in order to remove water and reduce the concentration of surface hydroxyl groups. Chemical treatment is generally capable of converting all water and hydroxyl groups in the oxide surface to relatively inert species. Useful chemical agents are for example, trimethylaluminum, ethyl magnesium chloride, chlorosilanes such as $SiCl_4$, disilazane, trimethylchlorosilane, dimethylaminotrimethylsilane and the like.

The chemical dehydration can be accomplished by slurrying the inorganic particulate material such as, for example silica, in an inert low boiling hydrocarbon, such as for example, hexane. During the chemical dehydration treatment, the silica should be maintained in a moisture and oxygen free atmosphere. To the silica slurry is then added a low boiling inert hydrocarbon solution of the chemical dehydrating agent, such as, for example dichloroldimethylsilane. The solution is added slowly to the slurry. The temperature ranges during chemical dehydration reaction can be from about 10° C. to about 120° C., however, higher and lower temperatures can be employed. Preferably, the temperature will be about 50° C. to about 100° C. The chemical dehydration procedure should be allowed to proceed until all the substantially reactive groups are removed from the particulate support material as indicated by cessation of gas evolution. Normally, the chemical dehydration reaction will be allowed to proceed from about 30 minutes to about 16 hours, preferably, 1 to 5 hours. Upon completion of the chemical dehydration, the solid particulate material may be filtered under a nitrogen atmosphere and washed one or more times with a dry, oxygen free inert solvent. The wash solvents, as well as the diluents employed to form the slurry and the solution of chemical dehydrating agent, can be any suitable inert hydrocarbon. Illustrative of such hydrocarbons are pentane, heptane, hexane, toluene, isopentane and the like.

Another chemical treatment that can be used on solid inorganic oxides such as silica involves reduction by contacting the solid with carbon monoxide at an elevated temperature sufficient to convert substantially all the water and hydroxyl groups to relatively inactive species.

The specific particle size of the support or inorganic oxide, surface area, pore volume, and number of hydroxyl groups is not considered critical to its utility in the practice of this invention. However, such characteristics often determine the amount of support to be employed in preparing the catalyst compositions, as well as affecting the particle morphology of polymers formed. The characteristics of the carrier or support must therefore be taken into consideration in choosing the same for use in the particular invention.

It is also within the scope of the present invention to add such a particulate solid to the liquid catalyst system after it has been formed and to carry out the prepolymerization in the presence of that solid.

The amount of cocatalyst and metallocene used in forming the liquid catalyst system for the prepolymerization can vary over a wide range depending upon the cocatalyst selected and the particular results desired. When aluminoxane is used, typically the molar ratio of aluminum in the aluminoxane to transition metal of the metallocene is in the range of about 1:1 to about 20,000:1, more preferably, a molar ratio of about 50:1 to about 2000:1 is used.

The prepolymerization is conducted in the liquid catalyst system, which can be a solution, a slurry, or a gel in a liquid. A wide range of olefins can be used for the prepolymerization. Typically, the prepolymerization will be conducted using an olefin, preferably selected from ethylene and non-aromatic alpha-olefins, and as propylene. It is within the scope of the invention to use a mixture of olefins, for example, ethylene and a higher alpha olefin can be used for the prepolymerization. The use of a higher alpha olefin, such as 1-butene, with ethylene is believed to increase the amount of copolymerization occurring between the olefin monomer and the olefinically unsaturated portion of the metallocene.

The prepolymerization can be conducted under relatively mild conditions. Typically, this would involve using low pressures of the olefin and relatively low temperatures designed to prevent site decomposition resulting from high concentrations of localized heat. The prepolymerization typically occurs at temperatures in the range of about −30° C. to about +110° C., more preferably in the range of about 0 to about +30° C. The amount of prepolymer can be varied but typically would be in the range of from about 1 to about 95 wt % of the resulting prepolymerized solid catalyst system, more preferably about 5 to 80 wt %. It is generally desirable to carry out the prepolymerization to at least a point where substantially all of the metallocene is in the solid rather than in the liquid since that maximizes the use of the metallocene.

After the prepolymerization, the resulting solid prepolymerized catalyst is preferably separated from the liquid of the reaction mixture. Various techniques known in the art can be used for carrying out this step. For example, the material could be separated by filtration, decantation, or by vacuum evaporation. It is currently preferred, however, not to rely upon vacuum evaporation since it is considered desirable to remove substantially all of the soluble components in the liquid reaction product of the prepolymerization from the resulting solid prepolymerized catalyst before it is stored or used for subsequent polymerization. After separating the solid from the liquid, the resulting solid is preferably washed with a hydrocarbon and then dried using high vacuum to remove substantially all the liquids and other volatile components that might still be associated with the solid. The vacuum drying is preferably carried out under relatively mild conditions, i.e. temperatures below 100° C. More typically the prepolymerized solid is dried by subjection to a high vacuum at a temperature of about 30° C. until a substantially constant weight is achieved. A preferred technique employs at least one initial wash with an aromatic hydrocarbon, such as toluene, followed by one or more washes with a paraffinic hydrocarbon, such as hexane, and then vacuum drying.

It is within the scope of the present invention to contact the prepolymerization reaction mixture product with a liquid in which the prepolymer is sparingly soluble, i.e. a counter solvent for the prepolymer, to help cause soluble prepolymer to precipitate from the solution. Such a liquid is also useful for the subsequent washing of the prepolymerized solid.

It is also within the scope of the present invention to add a particulate solid of the type aforementioned after the prepolymerization. Thus one can add the solid to the liquid prepolymerization product before the counter solvent is added. In this manner soluble prepolymer tends to precipitate onto the surface of the solid to aid in the recovery of the filtrate in a particulate form and to prevent agglomeration during drying. The liquid mixture resulting from the prepolymerization or the inventive solid prepolymerized catalyst can be subjected to sonification to help break up particles if desired.

Further, if desired, the recovered solid prepolymerized catalyst system can be screened to give particles having sizes that meet the particular needs for a particular type of polymerization.

Another option is to combine the recovered inventive solid prepolymerized catalyst system with an inert hydrocarbon, such as one of the type used as a wash liquid, and then to remove that liquid using a vacuum. In such a process, it is sometimes desirable to subject the resulting mixture to sonification before stripping off the liquid.

The solid prepolymerized catalyst system is suitable for use in the polymerization of olefinically unsaturated monomers. Such polymerizations can be carried out under gas phase, solution phase, or slurry phase conditions. The conditions used are as conventional. One difference is that generally it is not necessary to employ an additional cocatalyst with the solid prepolymerized catalyst.

In some cases it may be found desirable to employ small amounts of an organoaluminum compound as a scavenger for poisons. The term organoaluminum compounds include compounds such as triethylaluminum, trimethylaluminum, diethylaluminum chloride, ethylaluminum dichloride, ethylaluminum sesquichloride, and the like. Trialkylaluminum compounds are currently preferred. Also in some applications it may be desirable to employ small amounts of antistatic agents which assist in preventing the agglomeration of polymer particles during polymerization. Still further, when the inventive catalyst system is added to a reactor as a slurry in a liquid, it is sometimes desirable to add a particulate dried solid as a flow aid for the slurry. Preferably the solid has been dried using one of the methods described earlier. Inorganic oxides such as silica are particularly preferred. Currently, it is preferred to use a fumed silica such as that sold under the trade name Cab-o-sil. Generally the fumed silica is dried using heat and trimethylaluminum.

The polymers produced with the catalysts herein disclosed have a wide range of uses that will be apparent to those skilled in the art from the physical properties of the respective polymers. Applications such as molding, films, adhesives, and the like are indicated.

A further understanding of the present invention and its objects and advantages will be provided by the following example.

EXAMPLE I

Preparation of Oligomeric Metallocene

This procedure began with the metallocene 1-(9-fluorenyl)-1-(cyclopentadienyl)-1-(methyl)-1-(but-3-enyl) methane zirconium dichloride. First, 1.95 grams of that metallocene was placed in a glovebox. Then 80 mL of toluene was added and the tube was capped and taken out of a glovebox. The tube was then placed in a dry ice/isopropanol bath, i.e. about −78° C. and stirred for 10 minutes. Then, 5.16 mL of a 1.6 molar solution of butyllithium in hexane was added. The mixture was warmed up slowly and stirred overnight. The product was recovered by placing the tube back into the glovebox and filtering through sodium sulfate. The residue was washed with 30 mL of toluene and then dried using a vacuum. The process resulted in 1.2 grams of a black solid. The product can be described as an oligmeric metallocene reaction product. The metallocene product is believed to have an oligomeric structure so that it could be termed as inter-molecular metallocycle in contrast to the intra-molecular metallocycle that are obtained when n-butyllithium is reacted with metallocene having alkenyl groups attached to the cyclodienyl function of the metallocenes. The hydrogen NMR spectrum of this product provides evidence for the oligomeric structure because broad resonance signals are observed. The spectrum also shows the typical high field shifts for the carbon sigma bonds to the zirconium.

It is thus theorized that the product has repeating units of the formula

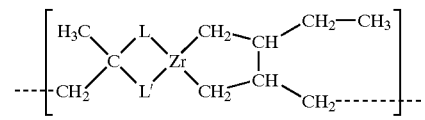

wherein L is 9-fluorenyl and L' is cyclopentadienyl.

EXAMPLE II

Preparation of a Solid Olefin Polymerization Catalyst System

In this case 50 mg of the oligomeric metallocene produced in Example I was placed in a serum bottle. This was combined with 10.5 mL of a liquid containing 10 weight percent aluminoxane, at least some of which was gelled. The resulting combination was stirred for 15 minutes. Then a suspension of silica in toluene was prepared by combining 2 grams of a trimethylaluminum dried Davison 952 silica into a serum bottle with 18 mL of toluene. The metallocene/ aluminoxane mixture in the first bottle was then poured into the silica suspension and stirred for 10 minutes. The bottle was capped and taken out of the dry box and suspended at room temperature in a water bath on a stir plate. Then the bottle contents were purged with ethylene for 1 minute. Then the contents were subjected to 4 psig of ethylene. After about 1 hour, the resulting particulate prepolymerized catalyst system was recovered by filtering using a high vacuum. The solid was then washed with toluene twice and then three times with hexane. The resulting pink solid was then dried in a vacuum.

EXAMPLE III

Polymerization

The solid catalyst system of Example II was then evaluated for its effectiveness in the polymerization of ethylene. The amount of catalyst employed was 0.0344 grams. The polymerization was conducted in a 1 gallon reactor in the presence of 2 liters of isobutane. The temperature was 90° C. The ethylene pressure was 450 psig. Hydrogen, 10 psig from a 300 cc vessel, was added to the reactor. The polymerization was conducted for one hour. 295.3 grams of polymer were recovered. The polymer had a $M_w$ of 103,000 g/ml and a $M_n$ of 35,300 g/ml. The activity of the catalyst in terms of grams of polyethylene per gram of solid catalyst was 8,600 grams of polyethylene per grams of solid catalyst per hour and 3,370 kg polyethylene per gram of zirconium per hour.

EXAMPLE IV

Preparation of Alternative Solid Catalyst System

In this case, 50 mg of the metallocene of Example I was placed in a serum bottle and 40 mL of toluene was added and the mixture was stirred for 10 minutes. Then 60 mL of tris(perfluorophenyl)borane was added and the mixture stirred for an additional 10 minutes. Then 2 grams of Davison 948 silica was added. The silica had been dried with trimethylaluminum. Then the slurry was stirred for an additional ten minutes. The bottle was capped and brought out of the glovebox. The bottle was then suspended in a 25° C. water bath on a stir plate. The bottle was then purged with ethylene and then subjected to prepolymerization using ethylene at 4 psig for about 1 hour. The liquid was filtered using a high vacuum. The solid was then put into a clean bottle and dried using a vacuum. The amount of particular solid catalyst obtained was 3.71 grams.

EXAMPLE V

Polymerization with the Alternative Catalyst System

The particulate solid catalyst system of Example IV was then evaluated for its effectiveness in the polymerization of ethylene. The amount used was 0.0948 grams. The polymerization was carried out using conditions as described in Example III. The polymerization produced an amount of polyethylene equivalent to 4,850 grams of polyethylene per grams of solid catalyst per hour which is equivalent to 1,805 kilograms of polyethylene per gram of zirconium per hour.

That which is claimed is:

1. A process for producing a metallocene useful as an olefin polymerization catalyst comprising reacting 1-(9-fluorenyl)-1-(cyclopentadienyl)-1-(methyl)-1-(but-3-enyl) methane zirconium dichloride with about two molar equivalents of n-butyl lithium in the absence of any other polymerizable composition.

2. A metallocene produced by the process of claim 1.

3. A catalyst system useful for the polymerization of olefins comprising the product resulting from the combination of the metallocene of claim 2 and an organometallic cocatalyst.

4. A catalyst system useful for the polymerization of olefins comprising the product prepared by combining the metallocene of claim 2 with an organometallic cocatalyst and conducting a prepolymerization in the presence of an olefin to produce a particulate prepolymerized catalyst system.

5. A catalyst system according to claim 4 wherein the cocatalyst comprises pentafluorophenyl borate.

6. A catalyst system according to claim 4 wherein the cocatalyst comprises an alkylaluminoxane.

7. A catalyst system prepared by dissolving the metallocene product of claim 2 in toluene, and adding tris (perfluorophenyl)borane and silica to the solution, and then conducting prepolymerization.

8. A catalyst system according to claim 7 wherein the olefin used in the prepolymerization consists essentially of ethylene.

9. A process for producing a polymer comprising contacting an olefin with the catalyst system of claim 8.

10. A process for producing a polymer comprising contacting an olefin with the catalyst system of claim 6.

* * * * *